United States Patent
Kuzma, Jr. et al.

(10) Patent No.: US 10,011,541 B2
(45) Date of Patent: Jul. 3, 2018

(54) RECOVERY OF ETHYLENE FROM METHANOL TO OLEFINS PROCESS

(71) Applicant: Lummus Technology Inc., Bloomfield, NJ (US)

(72) Inventors: Peter Daniel Kuzma, Jr., Bloomingdale, NJ (US); Stephen De Haan, Wayne, NJ (US); Daniel Lee Baumbach, Bloomfield, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 160 days.

(21) Appl. No.: 15/233,009

(22) Filed: Aug. 10, 2016

(65) Prior Publication Data

US 2016/0362352 A1    Dec. 15, 2016

Related U.S. Application Data

(62) Division of application No. 14/069,758, filed on Nov. 1, 2013, now Pat. No. 9,422,210.

(Continued)

(51) Int. Cl.
*C07C 7/04* (2006.01)
*C07C 7/08* (2006.01)
(Continued)

(52) U.S. Cl.
CPC .............. *C07C 7/005* (2013.01); *B01D 3/40* (2013.01); *B01D 53/1431* (2013.01); *B01D 53/1487* (2013.01); *C07C 1/20* (2013.01); *C07C 7/04* (2013.01); *C07C 7/08* (2013.01); *C07C 7/11* (2013.01); *F25J 3/0219* (2013.01); *F25J 3/0233* (2013.01); *F25J 3/0238* (2013.01); *F25J 2200/74* (2013.01); *F25J 2200/80* (2013.01); *F25J 2205/00* (2013.01);
(Continued)

(58) Field of Classification Search
CPC . C07C 1/20; F25J 3/0219; F25J 3/0233; F25J 3/0238
USPC ........................................................ 422/608
See application file for complete search history.

(56) References Cited

U.S. PATENT DOCUMENTS 3,607,734 A * 9/1971 Stafford, Sr. ............ C10G 5/04
                                                        208/341
4,167,402 A * 9/1979 Davis ...................... C07C 7/005
                                                        62/630

(Continued)

*Primary Examiner* — Huy Tram Nguyen
(74) *Attorney, Agent, or Firm* — Osha Liang LLP

(57) ABSTRACT

Olefins may be recovered from a methanol to olefins reactor effluent by initially feeding the effluent to an absorber demethanizer to contact the effluent with an absorbent to recover an overheads including methane and ethylene and a bottoms including the absorbent, ethylene, and ethane. The bottoms are separated to recover an ethylene fraction and an ethane fraction. The overheads are cooled and partially condensed in a first heat exchanger to a temperature of −40° C. or greater. The resulting stream, or a portion thereof, may be further cooled and condensed via indirect heat exchange with a mixed refrigerant to a temperature of less than −40° C. The non-condensed vapors are separated from the condensed liquids to form a liquid fraction and a methane fraction. The liquid fraction is fed to the absorber demethanizer as reflux, and the methane and ethane fractions combined to form the mixed refrigerant.

20 Claims, 2 Drawing Sheets

Related U.S. Application Data

(60) Provisional application No. 61/726,748, filed on Nov. 15, 2012.

(51) Int. Cl.
| | | |
|---|---|---|
| *C07C 7/11* | (2006.01) | |
| *C07C 1/20* | (2006.01) | |
| *F25J 3/00* | (2006.01) | |
| *C07C 7/00* | (2006.01) | |
| *B01D 3/40* | (2006.01) | |
| *B01D 53/14* | (2006.01) | |
| *F25J 3/02* | (2006.01) | |

(52) U.S. Cl.
CPC ........ *F25J 2205/04* (2013.01); *F25J 2205/50* (2013.01); *F25J 2205/90* (2013.01); *F25J 2215/02* (2013.01); *F25J 2215/62* (2013.01); *F25J 2270/02* (2013.01); *F25J 2270/88* (2013.01); *F25J 2270/90* (2013.01); *Y02P 30/42* (2015.11); *Y02P 30/464* (2015.11)

(56) References Cited

U.S. PATENT DOCUMENTS

| | | | | |
|---|---|---|---|---|
| 4,720,293 | A * | 1/1988 | Rowles | C07C 7/04 62/630 |
| 5,811,621 | A * | 9/1998 | van Dijk | B01D 3/009 203/73 |
| 5,960,643 | A * | 10/1999 | Kuechler | C07C 7/005 62/620 |
| 7,273,542 | B2 * | 9/2007 | Duhon | C10G 70/06 208/106 |
| 2004/0176646 | A1 * | 9/2004 | Van Egmond | C07C 7/04 568/699 |
| 2005/0033104 | A1 * | 2/2005 | van Egmond | C07C 7/11 585/800 |
| 2010/0105973 | A1 * | 4/2010 | De Haan | C07C 1/20 585/639 |
| 2010/0281915 | A1 * | 11/2010 | Roberts | C09K 5/041 62/612 |
| 2012/0167616 | A1 * | 7/2012 | Burger | F25J 1/0022 62/606 |
| 2012/0240615 | A1 * | 9/2012 | De Haan | C07C 1/20 62/600 |

\* cited by examiner

RECOVERY OF ETHYLENE FROM METHANOL TO OLEFINS PROCESS

CROSS-REFERENCE TO RELATED APPLICATIONS

This application, pursuant to 35 U.S.C. § 120, claims benefit to U.S. patent application Ser. No. 14/069,758 filed Nov. 1, 2013, now U.S. Pat. No. 9,422,210 which pursuant to 35 U.S.C. § 119(e), claims priority to U.S. Provisional Application Ser. No. 61/726,748, filed Nov. 15, 2012 Each of these applications is incorporated herein by reference in their entirety.

FIELD OF THE DISCLOSURE

In one aspect, embodiments disclosed herein relate to a process for converting an oxygenate to an olefin, such as a process for converting methanol to olefins (MTO) (oxygenate-to-olefin and methanol-to-olefin may be used interchangeably herein), and recovery of the olefins from the reactor effluent. In another aspect, embodiments disclosed herein relate to separating and recovering ethylene from an MTO reactor effluent using an absorbent to separate and recover ethylene from an MTO effluent, such as a $C_2$-$C_{10}$ hydrocarbon absorbent, in one or more extractive distillation and/or distillation stages, with efficient use of product streams to provide a mixed refrigerant that may be used to improved separations efficiency, increased ethylene recovery, reduce capital expenses (piece count), and/or reduced operating expenses (energy consumption, maintenance) in the olefin recovery process.

BACKGROUND

Limited availability and high cost of petroleum sources has led to the increased cost of producing basic commodity chemicals and their derivatives from such petroleum sources. As a result, various alternative competing technologies have been developed and commercially implemented in order to produce these chemicals from non-petroleum sources at a competitive cost.

One such technology involves catalytically converting methanol to olefins (MTO). Methanol is a readily available feedstock, which can be manufactured both from petroleum as well as non-petroleum sources, for example, by fermentation of biomass or from synthesis gas.

A typical MTO process, as disclosed in U.S. Pat. No. 4,499,327, which is hereby incorporated in its entirety, involves contacting methanol with a zeolite catalyst, such as an aluminosilicate, under conditions of temperature and pressure in order to produce light olefins, such as ethylene. Ethylene is an extremely valuable commodity chemical for producing various derivatives, such polyethylene, used in many commercial as well as consumer products and applications.

Before ethylene produced by an MTO process can be sold and used, it is necessary to employ a process which recovers the ethylene component in a desirable, ethylene rich stream by separating it from other components and impurities. For example, depending on the feedstock composition, the reaction conditions, and the extent of side reactions, an MTO effluent can contain other light olefins and diolefins, and light paraffins such as methane and ethane.

One process for the separating and recovering of ethylene from an MTO process effluent involves the use of flash stages and distillation at cryogenic temperatures, as described in U.S. Pat. No. 7,166,757 and U.S. Pat. No. 4,499,327. The cryogenic separation can be very expensive due to both the capital cost of the specialized vessel metallurgy and refrigeration equipment, and the operating costs, including compression and cooling for the energy-intensive chill train. The compression and cooling may be provided by, for example, an ethylene refrigerant provided by an ethylene refrigeration compressor from within the recovery unit or from another nearby processing unit. The cryogenic temperatures may also result in the undesirable formation of $N_2O_3$ from any NOx in the MTO process effluent.

Another process for separating and recovering ethylene from an MTO process effluent, at non-cryogenic temperatures, is disclosed in US20100105973. While operating at higher temperatures and potentially avoiding formation of $N_2O_3$, the higher operating temperatures may limit the extent of recovery of ethylene and propylene from the MTO effluent.

SUMMARY OF THE DISCLOSURE

In one aspect, embodiments disclosed herein relate to a process for recovery of the olefins from a methanol to olefins reactor effluent. The process may include: feeding an effluent from a methanol-to-olefins reactor system comprising methane, ethylene, and ethane to an absorber demethanizer; contacting at least a portion of the effluent with an absorbent in the absorber demethanizer to recover an overheads vapor fraction comprising methane and ethylene and a bottoms fraction comprising the absorbent, ethylene, and ethane; separating the bottoms fraction via one or more extractive distillation and/or distillation stages to recover an ethylene fraction and an ethane fraction; cooling and partially condensing the overheads vapor fraction in a first heat exchanger to a temperature of about −40° C. or greater; cooling and partially condensing at least a portion of the cooled and partially condensed overhead vapor fraction, via indirect heat exchange with a mixed refrigerant comprising methane and ethane, in a second heat exchanger to a temperature of less than about −40° C.; separating non-condensed vapors from the liquids condensed in the first and second heat exchangers to form an overhead liquid fraction and a methane fraction; feeding the overhead liquid fraction to the absorber demethanizer as a reflux; combining at least a portion of the methane and ethane fractions to form the mixed refrigerant.

In another aspect, embodiments disclosed herein relate to a process for recovery of the olefins from a methanol to olefins reactor effluent. The process may include: feeding an effluent from a methanol-to-olefins reactor system comprising methane, ethylene, and ethane to an absorber demethanizer; contacting at least a portion of the effluent with an absorbent in the absorber demethanizer to recover an overheads vapor fraction comprising methane and ethylene and a bottoms fraction comprising the absorbent, ethylene, and ethane; separating the bottoms fraction via one or more extractive distillation and/or distillation stages to recover an ethylene fraction and an ethane fraction; cooling and partially condensing the overheads vapor fraction in a first heat exchanger to a temperature of about −40° C. or greater; cooling and further condensing the cooled and partially condensed overhead vapor fraction, via indirect heat exchange with a mixed refrigerant comprising methane and ethane, in a second heat exchanger to a temperature of less than about −40° C.; separating liquids condensed in the first and second heat exchangers to form an overhead liquid fraction and a methane fraction; feeding the overhead liquid fraction to the absorber demethanizer as a reflux; and combining at least a portion of the methane and ethane fractions to form the mixed refrigerant.

In one aspect, embodiments disclosed herein relate to a process for recovery of the olefins from a methanol to olefins reactor effluent. The process may include: feeding an effluent from a methanol-to-olefins reactor system comprising methane, ethylene, and ethane to an absorber demethanizer; contacting at least a portion of the effluent with an absorbent in the absorber demethanizer to recover an overheads vapor fraction comprising methane and ethylene and a bottoms fraction comprising the absorbent, ethylene, and ethane; separating the bottoms fraction via one or more extractive distillation and/or distillation stages to recover an ethylene fraction and an ethane fraction; cooling and partially condensing the overheads vapor fraction in a first heat exchanger to a temperature of about −40° C. or greater; separating the cooled overheads vapor fraction to form a vapor fraction and a first overheads liquids fraction; cooling and partially condensing at least a portion of the vapor fraction, via indirect heat exchange with a mixed refrigerant comprising methane and ethane, in a second heat exchanger to a temperature of less than about −40° C.; separating the vapor fraction to form a methane fraction and a second overheads liquids fraction; feeding at least a portion of the first and second overheads liquid fractions to the absorber demethanizer as a reflux; and combining at least a portion of the methane and ethane fractions to form the mixed refrigerant.

In one aspect, embodiments disclosed herein relate to a process for recovery of light olefins from a mixed hydrocarbon stream. The process may include: feeding a mixed hydrocarbon stream comprising methane, ethylene, and ethane to an absorber demethanizer; contacting at least a portion of the effluent with an absorbent in the absorber demethanizer to recover an overheads vapor fraction comprising methane and ethylene and a bottoms fraction comprising the absorbent, ethylene, and ethane; separating the bottoms fraction via one or more extractive distillation and/or distillation stages to recover an ethylene fraction and an ethane fraction; cooling and partially condensing the overheads vapor fraction in a first heat exchanger to a temperature of about −40° C. or greater; cooling and partially condensing at least a portion of the cooled and partially condensed overhead vapor fraction, via indirect heat exchange with a mixed refrigerant comprising methane and ethane, in a second heat exchanger to a temperature of less than about −40° C.; separating non-condensed vapors from the liquids condensed in the first and second heat exchangers to form an overhead liquid fraction and a methane fraction; feeding the overhead liquid fraction to the absorber demethanizer as a reflux; and combining at least a portion of the methane and ethane fractions to form the mixed refrigerant.

In one aspect, embodiments disclosed herein relate to a system for the conversion of methanol to olefins and recovery of the olefins. The system may include: a methanol-to-olefins reactor system for converting methanol to a reactor effluent comprising methane, ethylene, and ethane; an absorber demethanizer for contacting at least a portion of the reactor effluent with an absorbent and to recover an overheads vapor fraction comprising methane and ethylene and a bottoms fraction comprising the absorbent, ethylene, and ethane; one or more extractive distillation and/or distillation stages for separating the bottoms fraction to recover an ethylene fraction and an ethane fraction; a first heat exchanger for cooling and partially condensing the overheads vapor fraction to a temperature of about −40° C. or greater; a second heat exchanger for cooling and partially condensing at least a portion of the cooled and partially condensed overhead vapor fraction via indirect heat exchange with a mixed refrigerant comprising methane and ethane, to a temperature of less than about −40° C.; a separator for separating non-condensed vapors from the liquids condensed in the first and second heat exchangers to form an overhead liquid fraction and a methane fraction; a flow line for feeding the overhead liquid fraction to the absorber demethanizer as a reflux; a flow line, vessel, or mixing chamber for combining at least a portion of the methane and ethane fractions to form the mixed refrigerant.

Other aspects and advantages will be apparent from the following description and the appended claims.

Figure 1:
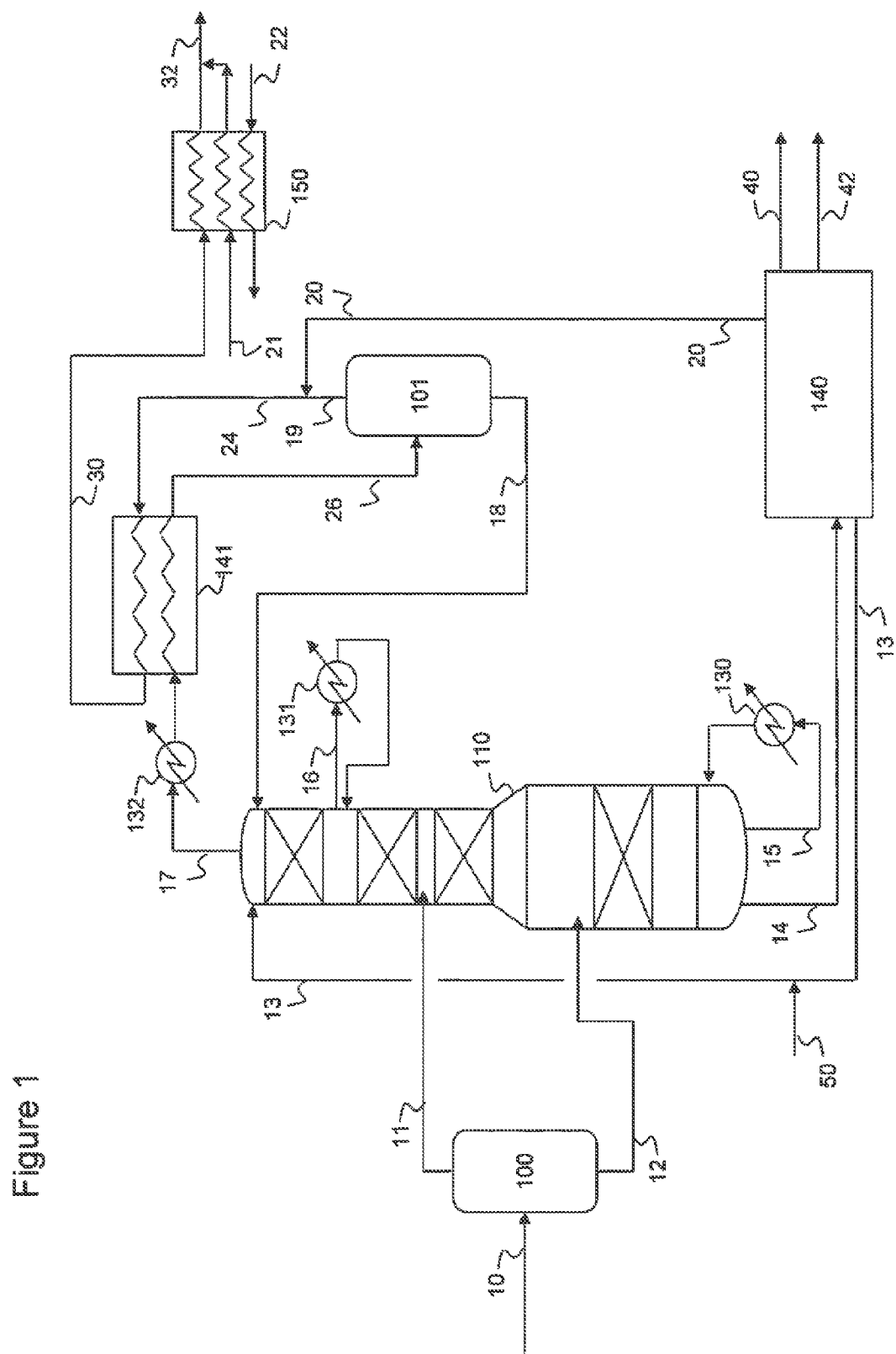
FIG. 1 is a simplified flow diagram of a process for converting oxygenates to olefins and recovering the olefins according to embodiments disclosed herein.

For simplicity, auxiliary equipment has been omitted from the figures. One of ordinary skill in the art would recognize that other equipment and devices, including but not limited to, pumps, compressors, heat exchangers, drums, vessels, reactors, flow lines, valves, and control loops, may also be used although not explicitly illustrated.

DETAILED DESCRIPTION

In one aspect, embodiments disclosed herein relate to a process for converting an oxygenate to an olefin, such as a process for converting methanol to olefins (MTO) (oxygenate-to-olefin and methanol-to-olefin may be used interchangeably herein), and recovery of the olefins from the reactor effluent. In another aspect, embodiments disclosed herein relate to separating and recovering ethylene from an MTO reactor effluent using an absorbent to separate and recover ethylene from an MTO effluent, such as a $C_2$-$C_{10}$ hydrocarbon absorbent, in one or more extractive distillation and/or distillation stages, with efficient use of product streams to provide a mixed refrigerant that may be used to improved separations efficiency, increased ethylene recovery, reduce capital expenses (piece count), and/or reduced operating expenses (energy consumption, maintenance) in the olefin recovery process.

Processes disclosed herein may be used to convert oxygenates to olefins and to recover the olefins. For example, processes disclosed herein may be used to convert methanol to olefins, and to separate and recover ethylene from the methanol-to-olefins reaction effluent.

Various feedstocks containing one or more oxygenated compounds may be converted to one or more olefins. Non-limiting examples of suitable oxygenate compounds include alcohols, including straight and branched chain aliphatic alcohols and their unsaturated counterparts, such as methanol, ethanol, n-propanol and isopropanol; alkyl ethers such as dimethyl ether, diethyl ether, methylethyl ether and di-isopropyl ether; alkyl ketones such as dimethylketone; aldehydes such as formaldehydes, dimethylcarbonate and various acids such as acetic acid. In some embodiments, the oxygenate feedstock may include methanol as the main oxygenate compound. In other embodiments, the oxygenated feedstock may consist essentially of methanol.

In addition to oxygenated compounds, such as methanol, the feedstock may contain one or more diluent(s), which are generally non-reactive to the feedstock or the catalyst and are typically used to reduce the concentration of reactants in the feedstock. Non-limiting examples of diluents include helium, argon, nitrogen, carbon monoxide, carbon dioxide, water, essentially non-reactive paraffins, such as methane, ethane, and propane, essentially non-reactive aromatic compounds, and mixtures thereof. In some embodiments, a diluent may include at least one of nitrogen and water. In other embodiments, a diluent may consist essentially of nitrogen. Additionally, air may be entrained into the methanol-to-olefins reaction system, for example, due to operation under partial vacuum conditions or as an impurity in one of the feedstock components.

Any oxygenate-to-olefin or methanol-to-olefins reaction system may be used to produce olefins for processes herein. In some embodiments, the methanol-to-olefins reactor system may include a single reaction zone. In other embodiments, the methanol-to-olefins reactor system may comprise multiple reaction zones arranged in series. In some embodiments, the methanol may travel upflow through the one or more reaction zones. In other embodiments, the methanol may travel downflow through the one or more reaction zones.

One or a combination of a variety of reactor types can be used in the methanol-to-olefins reactor system, including, but not limited to fixed bed reactors; dense, bubbling, riser-type, or slurry-type fluidized bed reactors; boiling point reactors; and catalytic distillation reactors, for example, as described in U.S. Pat. Nos. 4,076,796 and 6,287,522. One of ordinary skill in the art would recognize that other types of reactors can also be used.

The catalyst used in the methanol-to-olefins reactor system may be one of a homogeneous catalyst or a heterogeneous catalyst. In some embodiments, the catalyst may be a zeolite or mole sieve catalyst. In one specific embodiment, the catalyst may be a crystalline aluminosilicate zeolite catalyst, such as those disclosed in U.S. Pat. Nos. 4,062,905, 4,079,095, 3,911,041, and 4,049,573. One of ordinary skill in the art would recognize that other types of catalysts can also be used.

The methanol-to-olefins reaction may be conducted over a wide range of temperatures, such as in the range from about 200° C. to about 1000° C. In some embodiments, the temperature of the methanol-to-olefins reaction system may be in the range from about 200° C. to about 700° C. In other embodiments, the temperature of the methanol-to-olefins reaction system may be in the range from about 300° C. to about 600° C. In yet other embodiments, the temperature of the methanol-to-olefins reaction system may be in the range from about 350° C. to about 550° C.

Similarly, the process can be conducted over a wide range of pressures including autogenous pressure. Typical partial pressures of the feedstock, exclusive of any diluent therein employed in the process, may be in the range from about 0.1 kPaa to about 5 MPaa. In some embodiments, the pressure of the methanol-to-olefins reaction system may be in the range from about 5 kPaa to about 1 MPaa. In other embodiments, the pressure of the methanol-to-olefins reaction system may be in the range from about 20 kPaa to about 500 kPaa.

The olefins produced by a process for producing olefins from oxygenates, for example a methanol-to-olefins process, according to embodiments disclosed herein may include one or more of $C_2$ to $C_3$ olefins and/or diolefins. In some embodiments, the olefins produced may include one or more of $C_2$ to $C_5$ olefins. In other embodiments, the olefins produced may include one or more of $C_2$ to $C_6$ olefins. In yet other embodiments, the olefins produced may include one or more of $C_2$ to $C_4$ olefins, for example, ethylene and propylene. In still other embodiments, the olefins produced may consist essentially of ethylene.

In some embodiments, the concentration of ethylene in the methanol-to-ethylate reactor effluent may be at least approximately 5 mole percent. In other embodiments, the concentration of ethylene in the methanol-to-ethylene reactor effluent may be at least approximately 10 mole percent. In yet other embodiments, the concentration of ethylene in the methanol-to-ethylene reactor effluent may be at least approximately 20 mole percent. In still other embodiments, the concentration of ethylene in the methanol-to-ethylene reactor effluent may be at least approximately 30 mole percent.

A methanol-to-olefins reaction may also produce non-olefin products, including but not limited to, paraffins, acetylenes, ethers, and esters. For example, a methanol-to-olefins reaction effluent may include methane, ethane, propane, n-butane, isobutane, nm butene, isobutene, butadiene, dimethyl ether and water. The presence and concentrations of these by-products may vary depending, for example, on the feedstock qualify, the type and size of reactor, the reaction conditions, and the type and condition of the catalyst used.

In some embodiments, the concentration of methane in the methanol-to-ethylene reactor effluent may be less than approximately 30 mole percent. In other embodiments, the concentration of methane in the methanol-to-ethylene reactor effluent may be less than approximately 20 mole percent. In yet other embodiments, the concentration of methane in the methanol-to-ethylene reactor effluent may be less than approximately 10 mole percent. In still other embodiments, the concentration of methane in the methanol-to-ethylene reactor effluent may be less than approximately 5 mole percent. In other embodiments, the concentration of methane in the methanol-to-ethylene reactor effluent may be less than approximately 2 mole percent.

In order to recover ethylene of sufficient purity, the methanol-to-olefins reactor effluent may b processed in one or more separation stages. For example, it may be desired or necessary to separate ethylene from various reactants and products, including but not limited to, ethers and alcohols, carbon dioxide, water, methane, ethane, and other reactants, reaction products, and diluents.

In some embodiment, at least a portion of the methanol-to-olefins reactor effluent may be fed to an extraction system for removing any methanol and/or ethers contained therein using an aqueous solvent, such as water or glycol. An aqueous fraction having an increased concentration of methanol and ethers may be recovered from the extraction system. A hydrocarbon phase comprising methane and ethylene, and lean in methanol and ethers, may be recovered from the reactor effluent in the extraction system. The hydrocarbon phase may then be sent for further component separation(s). In some embodiments, the methanol-to-olefins reactor effluent may be compressed prior to any further separation(s).

Carbon dioxide that may be present in the methanol-to-olefins reactor effluent may also require removal. For example, an olefin product specification may require removal of carbon dioxide from the methanol-to-olefins reactor effluent. Further, exposure of the carbon dioxide containing stream to below-sublimation temperatures may result in equipment damage and frozen piping. Methods commonly known and used in the industry, such as caustic solution treatment or amine absorption, may be used to remove $CO_2$ from the methanol-to-olefins reactor effluent. In some embodiments, the reactor effluent may be contacted with a caustic solution to separate at least a portion of the carbon dioxide present in the reactor effluent. If necessary, the reactor effluent may be compressed prior to the carbon dioxide removal stage.

The presence of water in methanol-to-olefins reaction effluent can lead to a number of problems. For example, cooling and/or compressing the reaction effluent may result in formation of water condensate that can damage equipment and freeze pipes. Therefore, dehydration of the reactor effluent to remove water using one of a number of techniques commonly used in the industry may be required or may be optionally performed based on process schemes and temperatures employed. In some embodiments, a molecular sieve dryer may be used for separating at least a portion of the water, drying the reactor effluent. In other embodiments, a chemical desiccant such as glycol may be used for drying the reactor effluent. In yet other embodiments, a portion of the water in the reactor effluent may be condensed and the remaining effluent may be dried. Other dehydration techniques commonly known and used in the industry may also be used. If necessary, the reactor effluent may be compressed prior to the water removal stage.

Following compression, acid gas removal, drying, and chilling, the MTO effluent may be fed to a separation train to recover the various products, such as ethylene, propylene, ethane, and others. The separation train may include an absorber demethanizer for separation of ethylene and heavier hydrocarbons from methane. A hydrocarbon absorbent, such as a $C_2$-$C_{10}$ hydrocarbon absorbent, can be effectively used as an absorbent to separate and recover ethylene and higher olefinic hydrocarbons from an MTO reaction effluent. For example, an MTO reaction effluent including ethylene and methane can be contacted with a hydrocarbon absorbent in an extraction distillation system, whereby at least a portion of the ethylene is absorbed by the hydrocarbon absorbent. In some embodiments, the hydrocarbon absorbent may be a $C_2$ to $C_4$ hydrocarbon, for example, including at least one of ethane, propane, propylene, n-butane, isobutane, n-butene, and isobutane. In other embodiments, the hydrocarbon absorbent may consist essentially of propane. Other absorbents, hydrocarbon and non-hydrocarbon, may also be used, and while not explicitly listed above, are contemplated for use as an absorbent for performing the desired separation of ethylene from MTO effluents according to embodiments herein.

In some embodiments, the absorber demethanizer may include one or more extractive distillation and/or distillation stages. The one or more extractive distillation and/or distillation stages may comprise trays and/or packing for providing a sufficient surface for contact of the absorbent with the MTO reactor effluent. In some embodiments, the methanol-to-olefins reactor effluent and hydrocarbon absorbent may be contacted counter-currently in the absorber demethanizer.

In some embodiments, the absorber demethanizer and the associated overheads system may be operated at an overheads temperature of greater than about −90° C., thereby limiting the formation of $N_2O_3$. In other embodiments, the absorber demethanizer system may be operated at an overheads temperature of approximately −80° C. or greater; −70° C. or greater in yet other embodiments. In general, the overheads pressure inside the absorber demethanizer may be maintained at a level required for the distillation and as required for absorption of ethylene into the absorbent. In some embodiments, the absorber demethanizer may be operated at an overheads pressure in the range from approximately 0.01 MPag to 10 MPag; in the range from about 0.1 MPag to about 4 MPag in other embodiments; and in the range from about 0.5 MPag to about 3 MPag in other embodiments.

In some embodiments, at least approximately 70 percent of ethylene molecules in the MTO reactor effluent may be absorbed by the absorbent in the absorber demethanizer and recovered from the absorber demethanizer as a bottoms fraction along with the hydrocarbon absorbent. In other embodiments, at least approximately 80 percent of ethylene molecules may be absorbed and recovered from the absorber demethanizer as a bottoms fraction along with the hydrocarbon absorbent. In yet other embodiments, at least approximately 90 percent of ethylene molecules may be absorbed and recovered from the absorber demethanizer as a bottoms fraction along with the hydrocarbon absorbent. In still other embodiments, at least approximately 95 percent of ethylene molecules may be absorbed and recovered from the absorber demethanizer as a bottoms fraction along with the hydrocarbon absorbent. In other embodiments, at least approximately 99 percent of ethylene molecules may be absorbed and recovered from the absorber demethanizer as a bottoms fraction along with the hydrocarbon absorbent.

The bottoms fraction may be further separated to recover ethylene and other products. For example, the recovered ethylene, propylene and ethane in the bottoms fraction recovered from the absorber demethanizer may be separated into an ethylene product, a propylene product, and ethane product. In some embodiments, the bottoms fraction may be separated to form an ethylene fraction and a hydrocarbon fraction including at least one of $C_2$-$C_4$ hydrocarbon heavier than ethylene. In other embodiments, the bottoms fraction may be separated to form light hydrocarbon fraction containing ethylene and ethane, and a hydrocarbon fraction containing at least one $C_3$-$C_4$ hydrocarbon. The $C_2$-$C_4$ hydrocarbon fraction or the ethylene/ethane fraction may subsequently be separated to recover an ethane fraction, resulting in a methane product, the overheads fraction recovered from the absorber demethanizer, and an ethane product, recovered via separation of the absorber demethanizer bottoms fraction.

The overhead fraction recovered from the absorber demethanizer may be cooled and partially condensed, providing reflux to the absorber demethanizer and limiting the amount of ethylene and heavier hydrocarbons in the resulting methane product stream. Cooling and partial condensation may be achieved according to embodiments herein using a first exchanger to reduce the temperature of the overhead stream to a first temperature, and a second exchanger to further reduce the temperature. For example, the first exchanger may, via indirect heat exchange with a propane or propylene refrigerant, reduce the temperature of the overhead fraction to a temperature greater than about −40° C. The resulting stream may then be further cooled to a temperature of less than −40° C. via indirect heat exchange against a mixture of the methane product stream and the ethane product stream, or portions thereof. Combining these two streams before reheating them may provide more heat recovery at lower temperatures than can be achieved by reheating the streams individually. The temperature of the combined stream is low enough that it can be used to cool the absorber demethanizer overhead from the condenser to below −40° C. This lower temperature condenses more of the ethylene, propylene and ethane present in the absorber demethanizer overhead and the condensed liquid is collected in the demethanizer reflux drum and sent back to the demethanizer as reflux.

Referring now to FIG. 1, a process for converting methanol to olefins and subsequently recovering ethylene according to embodiments disclosed herein is illustrated. As noted above, methanol may be supplied to a methanol-to-olefins reactor system (not illustrated), where the methanol may be contacted with a catalyst at conditions of temperature and pressure inside the methanol-to-olefins reactor system to produce ethylene and/or other olefins. A methanol-to-olefins reactor effluent may then be recovered from the methanol-to-olefins reactor system and, depending on the specific process requirements, the methanol-to-olefins reactor effluent may undergo various processes to remove one or more of ethers and alcohols, carbon dioxide, and water from the reactor effluent.

The reactor effluent, after compression, acid gas removal, drying, and chilling enters the demethanizer feed drum 100 as stream 10. The feed is split into vapor stream 11 and liquid stream 12, each of which is fed to absorber demethanizer 110. Absorbent fed via wash stream 13 enters the top of absorber demethanizer 110 to facilitate the recovery of ethylene and propylene. The $C_2$ (ethylene and ethane) and heavier components in the feed are absorbed in the absorbent and recovered as bottoms fraction 14. Heat may be added to absorber demethanizer 110 via reboiler(s) 130 via indirect heat exchange between one or more process or utility streams and reboiler circulation stream 15. Bottoms fraction 14 is then processed in one or more distillation columns in separation zone 140 to recover absorbent 13, ethane 20, ethylene 40, and one or more additional hydrocarbon products 42 (such as propylene and higher olefins or other paraffinic hydrocarbons).

To remove a portion of the heat of absorption when ethylene and propylene in the feed condense in the absorbent, a side draw 16 is withdrawn from absorber demethanizer 110 and chilled against refrigerant or process streams in exchanger 131 before being returned to the absorber demethanizer 110. The gross overhead vapor fraction 17 withdrawn from absorber demethanizer 110 is cooled and partially condensed against refrigerant or process streams in heat exchanger 132.

Gross overhead vapor fraction 17 is then further cooled and condensed, such as to a temperature below about −40° C., in heat exchanger 141, such as a brazed aluminum heat exchanger, via indirect heat exchange with a mixed refrigerant 24, obtained by mixing the demethanizer net overhead stream 19 (methane) with the ethane product 20 (obtained via separation of ethane from other components in bottoms fraction 14, as noted above). When mixed refrigerant 24 is vaporized in exchanger 141, the gross overhead vapor fraction 17 may be cooled to a temperature below −40° C., condensing additional ethylene and propylene contained in the gross overhead. The cooled and condensed exchanger effluent 26 may then be separated in reflux drum 101 into a net overhead stream 19 (primarily methane as the hydrocarbon component) and reflux stream 18. The heated mixed refrigerant may be recovered from heat exchanger 141 via flow line 30.

If desired, the heated mixed refrigerant in line 30 may be used to cool other process streams in heat exchanger 150. For example, mixed refrigerant 30 may be used to cool various process or refrigerant streams 22. Additional streams 21 may also be used provide cooling in exchanger 150. The reheated offgas streams 21, 30 from heat exchanger 150 may then be combined and exported as fuel gas via flow line 32.

Figure 2:
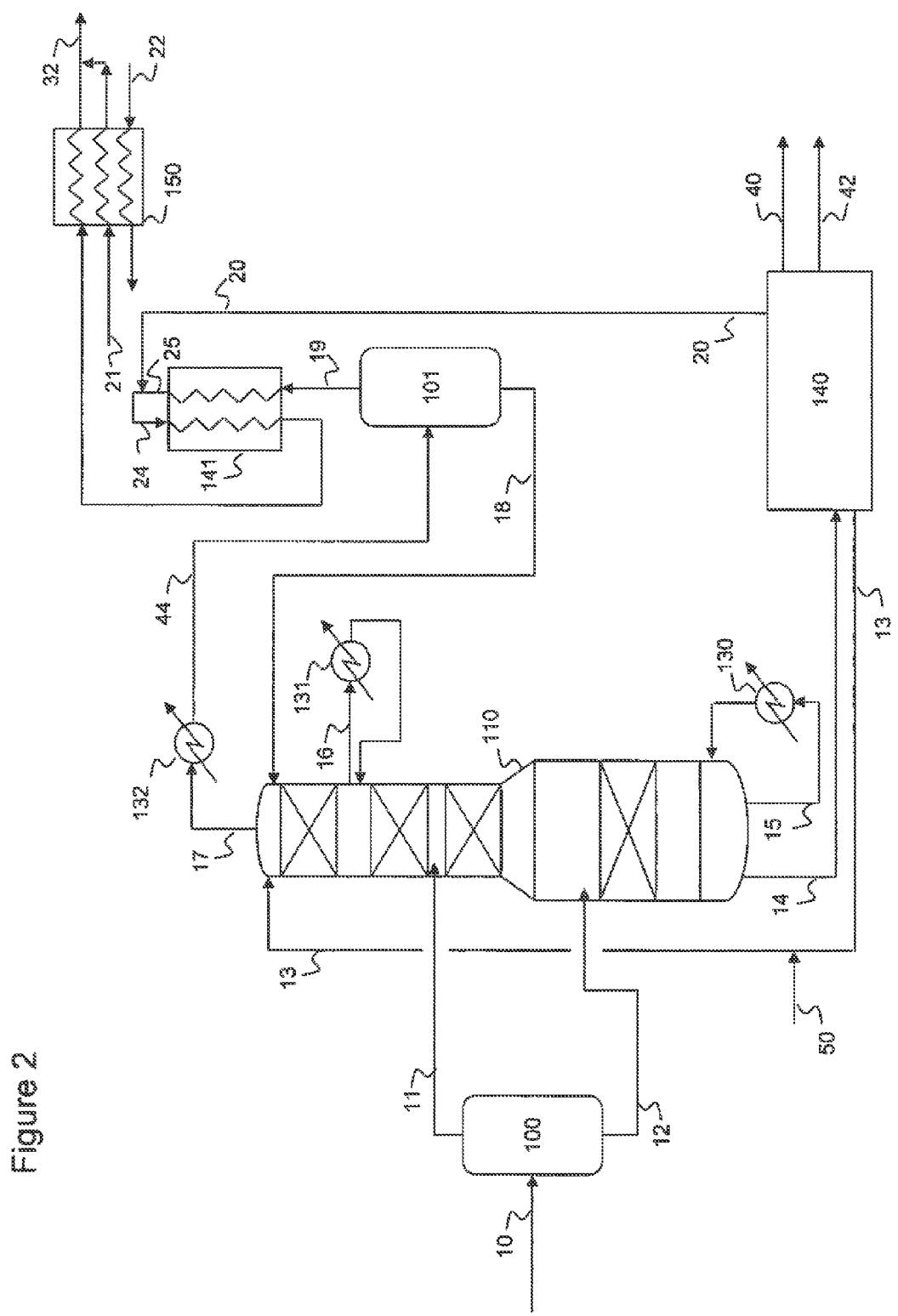
FIG. 2 is a simplified process flow diagrams of processes according to embodiments disclosed herein.

The cooling capacity of the ethane product stream may also be recovered as illustrated in FIG. 2, where like numerals represent like parts. Processing in absorber demethanizer 110 and separation zone 140 is as described above with respect to FIG. 1. In this embodiment, the gross overhead vapor fraction 17 is cooled and partially condensed in exchanger 132. The cooled and condensed overheads in stream 44 are then fed to reflux drum 101 for separation into net overheads 19 and reflux stream 18. The net overhead 19 is then further condensed in heat exchanger 141. The condensate resulting from cooling of net overhead stream 19 may be separated in a separation drum (not shown) or inside heat exchanger 141 by fallback (as illustrated, resulting in a chilled net vapor stream 25). Chilled net vapor stream 25 may be mixed with ethane product 20 to result in mixed refrigerant 24, used as the heat exchange medium in exchanger 141. The warmed mixed refrigerant may then optionally be used as a heat exchange medium in exchanger 150 and sent to fuel, as discussed above.

With regard to separation zone 140, the particular distillation columns, extractive distillation columns, or other separators used to recover the various products may depend upon the type of oxygenate used in the oxygenate to olefins reactor, the mixture of products obtained from the oxygenate to olefins reactor, and desired products or product mixtures, among other factors. In some embodiments, such as where the absorbent is propane, separation zone 140 may include a demethanizer for separating C2's from C3's and heavier components, a depropanizer for separating C3's from C4's and heavier hydrocarbons, a deethylenizer for separating ethane from ethylene, and a depropylenizeer for separating propane from propylene. The propane absorbent, recovered as a liquid bottoms from the depropylenizer, may then be recycled for use in absorber demethanizer 110. Fresh propane may be added or excess propane withdrawn, as necessary, via flow line 50. In this manner, ethane is recovered from the deethylenizer as a liquid bottoms and may be flashed to provide cooling in exchanger 141, as described above. Other various combinations of distillation columns and separators may also be used to result in the desired products.

As described above, embodiments described herein provide for formation of a mixed refrigerant from methane and ethane products generated by a methanol-to-olefins process and recovered via downstream separation units. Use of the mixed refrigerant may provide additional cooling capacity at lower temperatures than can be achieved via the methane and ethane product streams individually. Further, the temperature of the mixed refrigerant may be sufficiently low that when used to cool the absorber demethanizer overheads, temperature of less than −40° C. may be achieved, which is lower than a propane or propylene refrigerant may achieve. This lower temperature condenses additional ethylene, propylene, propane and ethane present in the demethanizer overheads, providing additional reflux capacity and increased hydrocarbon recover. Such benefits may be achieved without additional compressors and energy consumption typically required to provide refrigeration at temperatures less then −40° C.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A system for the conversion of methanol to olefins and recovery of the olefins, the system comprising:
    a methanol-to-olefins reactor system for converting methanol to a reactor effluent comprising methane, ethylene, and ethane;
    an absorber demethanizer for contacting at least a portion of the reactor effluent with an absorbent and to recover an overheads vapor fraction comprising methane and ethylene and a bottoms fraction comprising the absorbent, ethylene, and ethane;
    one or more extractive distillation and/or distillation stages for separating the bottoms fraction to recover an ethylene fraction and an ethane fraction;
    a first heat exchanger for cooling and partially condensing the overheads vapor fraction to a temperature of about −40° C. or greater;
    a second heat exchanger for cooling and partially condensing at least a portion of the cooled and partially condensed overhead vapor fraction via indirect heat exchange with a mixed refrigerant, to a temperature of less than about −40° C.;
    a separator for separating non-condensed vapors from the liquids condensed in the first and second heat exchangers to form an overhead liquid fraction and a methane fraction;
    a flow line for feeding the overhead liquid fraction to the absorber demethanizer as a reflux;
    a flow line, vessel, or mixing chamber for combining at least a portion of the methane and ethane fractions to form the mixed refrigerant.

2. The system of claim 1, further comprising a caustic solution treatment system or an amine absorption system for removing carbon dioxide from the methanol-to-olefins reactor effluent or a portion thereof.

3. The system of claim 2, further comprising a compressor for compressing the methanol-to-olefins reactor effluent upstream of the caustic solution treatment system or the amine absorption system.

4. The system of claim 1, further comprising a molecular sieve dryer or a dehydration system for removing water from the methanol-to-olefins reactor effluent or a portion thereof.

5. The system of claim 1, further comprising a heat exchanger for cooling the methanol-to-olefins reactor effluent upstream of the absorber demethanizer.

6. The system of claim 1, further comprising:
    a feed drum for splitting the methanol-to-olefins reactor effluent into a feed vapor stream and a feed liquid stream;
    a flow line for supplying the feed vapor stream to an upper portion of the absorber demethanizer; and
    a flow line for supplying the feed liquid stream to a lower portion of the absorber demethanizer.

7. The system of claim 1, further comprising a side draw, a heat exchanger, and a return line for withdrawing a stream from, cooling, and returning the stream to the absorber demethanizer.

8. The system of claim 1, wherein the second heat exchanger comprises a brazed aluminum heat exchanger.

9. The system of claim 1, further comprising:
    a flow line for recovering heated mixed refrigerant from the second heat exchanger; and
    a third heat exchanger for cooling one or more additional streams via indirect heat exchange with the heated mixed refrigerant.

10. A system for the recovery of the olefins, the system comprising:
    an absorber demethanizer for contacting a stream comprising methane, ethylene, and ethane with an absorbent and to recover an overheads vapor fraction comprising methane and ethylene and a bottoms fraction comprising the absorbent, ethylene, and ethane;
    one or more extractive distillation and/or distillation stages for separating the bottoms fraction to recover an ethylene fraction and an ethane fraction;
    a first heat exchanger for cooling and partially condensing the overheads vapor fraction to a temperature of about −40° C. or greater;
    a second heat exchanger for cooling and partially condensing at least a portion of the cooled and partially condensed overhead vapor fraction via indirect heat exchange with a mixed refrigerant to a temperature of less than about −40° C.;
    a separator for separating non-condensed vapors from the liquids condensed in the first and second heat exchangers to form an overhead liquid fraction and a methane fraction;
    a flow line for feeding the overhead liquid fraction to the absorber demethanizer as a reflux;
    a flow line, vessel, or mixing chamber for combining at least a portion of the methane and ethane fractions to form the mixed refrigerant.

11. The system of claim 10, further comprising a heat exchanger for cooling the methanol-to-olefins reactor effluent upstream of the absorber demethanizer.

12. The system of claim 10, further comprising:
    a feed drum for splitting the methanol-to-olefins reactor effluent into a feed vapor stream and a feed liquid stream;
    a flow line for supplying the feed vapor stream to an upper portion of the absorber demethanizer; and
    a flow line for supplying the feed liquid stream to a lower portion of the absorber demethanizer.

13. The system of claim 10, further comprising a side draw, a heat exchanger, and a return line for withdrawing a stream from the absorber demethanizer, cooling the stream, and returning the stream to the absorber demethanizer.

14. The system of claim 10, further comprising:
    a flow line for recovering heated mixed refrigerant from the second heat exchanger; and
    a third heat exchanger for cooling one or more additional streams via indirect heat exchange with the heated mixed refrigerant.

15. A system for recovery of the olefins from a methanol to olefins reactor effluent, the system comprising:
    an absorber demethanizer for contacting a stream comprising methane, ethylene, and ethane with an absorbent and to recover an overheads vapor fraction comprising methane and ethylene and a bottoms fraction comprising the absorbent, ethylene, and ethane;
    a separation system for separating the bottoms fraction via one or more extractive distillation and/or distillation stages to recover an ethylene fraction and an ethane fraction;
    a first heat exchanger for cooling and partially condensing the overheads vapor fraction to a temperature of about −40° C. or greater;
    a separator for separating the cooled overheads vapor fraction to form a vapor fraction and a first overheads liquids fraction;
    a second heat exchanger for cooling and partially condensing at least a portion of the vapor fraction, via indirect heat exchange with a mixed refrigerant, to a temperature of less than about −40° C.;

a separator for separating the vapor fraction to form a methane fraction and a second overheads liquids fraction;

a flow line for feeding at least a portion of the first and second overheads liquid fractions to the absorber demethanizer as a reflux;

a flow line, vessel, or mixing chamber for combining at least a portion of the methane and ethane fractions to form the mixed refrigerant.

16. The system of claim 15, wherein the second heat exchanger and the separator for separating the vapor fraction are integral.

17. The system of claim 15, further comprising:
a flow line for recovering heated mixed refrigerant from the second heat exchanger; and
a third heat exchanger for cooling one or more additional streams via indirect heat exchange with the heated mixed refrigerant.

18. The system of claim 15, wherein the separation system for separating the bottoms fraction comprises one or more of a deethanizer, a depropanizer, or a deethylenize.

19. The system of claim 18, further comprising a flow line for recovering propane from the depropanizer and for feeding the recovered propane, or a portion thereof, to the absorber demethanizer as the absorbent.

20. The system of claim 18, further comprising a flow line for recovering the ethane fraction as a bottoms from the deethylenizer.

* * * * *